United States Patent
Nouadje et al.

(10) Patent No.: US 6,572,746 B1
(45) Date of Patent: Jun. 3, 2003

(54) COMPOSITIONS FOR THE REHYDRATATION OF AN ELECTROPHORESIS SUPPORT IN ORDER TO IMPROVE ZONE ELECTROPHORESIS

(75) Inventors: Georges Nouadje, Evry (FR); Laurent Vincent, Bondoufle (FR)

(73) Assignee: Sebia (FR)

( * ) Notice: Subject to any disclaimer, the term of this patent is extended or adjusted under 35 U.S.C. 154(b) by 364 days.

(21) Appl. No.: 09/589,008

(22) Filed: Jun. 7, 2000

(30) Foreign Application Priority Data

Feb. 22, 2000 (FR) ............................................ 00 02206

(51) Int. Cl.⁷ .............................................. G01N 27/26
(52) U.S. Cl. ..................... 204/409; 204/616; 204/606
(58) Field of Search ................................ 204/409, 606, 204/616

(56) References Cited

U.S. PATENT DOCUMENTS

| | | | | |
|---|---|---|---|---|
| 3,482,943 A | * | 12/1969 | Csizmas et al. ............... | 23/253 |
| 3,932,229 A | | 1/1976 | Grandine .................... | 204/180 |
| 5,064,519 A | | 11/1991 | Tice, Jr. et al. .......... | 204/182.8 |
| 5,405,516 A | | 4/1995 | Bellon ...................... | 204/180.1 |
| 5,464,515 A | | 11/1995 | Bellon ...................... | 204/182.8 |
| 5,681,437 A | * | 10/1997 | Black et al. ................ | 204/456 |
| 5,683,915 A | * | 11/1997 | Black et al. ................ | 422/100 |
| 5,840,338 A | * | 11/1998 | Roos et al. ................. | 424/484 |
| 5,993,627 A | | 11/1999 | Anderson et al. ........... | 204/456 |
| 6,231,813 B1 | * | 5/2001 | Ally et al. .................. | 204/456 |
| 6,232,076 B1 | * | 5/2001 | Schulz .......................... | 435/6 |

FOREIGN PATENT DOCUMENTS

| EP | 0 493 996 A1 | 12/1991 | ........... B01D/57/02 |
|---|---|---|---|
| FR | 2 347 674 | 4/1976 | |
| WO | WO 99/33550 | 7/1999 | |

OTHER PUBLICATIONS

Daniel Harris, Quantitative Chemical Analysis, 4th Ed., W. H. Freeman and Company, NY, 1995; table 11–1, chapter 11–6, chapter 11–7, box 11–3.*

Voet and Voet, Biochemistry, John Wiley and Sons, NY, 1990; chapter 4–1, figure 4–21, chapter 5–4, chapter 6–2.*

Van Hoof V.O., De Broe Marc E., Clinical Laboratory Sciences, vol. 31, issue 3 p. 197–293 (1994) "Interpretation and clinical significance of alkaline phosphatase isoenzyme patterns."

* cited by examiner

Primary Examiner—Jill Warden
Assistant Examiner—Jennine Brown
(74) Attorney, Agent, or Firm—Lerner, David, Littenberg, Krumholz & Mentlik, LLP

(57) ABSTRACT

The invention concerns a composition for use in a process for separating the constituents of a sample by electrophoresis on an electrophoresis support, comprising one or more ionic compounds which, on applying an electric field to an electrophoresis support having negative surface charges, causes hydration of the zone for loading the sample to be separated when said zone carries a compression mark resulting from loading the sample.

35 Claims, No Drawings

COMPOSITIONS FOR THE REHYDRATATION OF AN ELECTROPHORESIS SUPPORT IN ORDER TO IMPROVE ZONE ELECTROPHORESIS

BACKGROUND OF THE INVENTION

Zone electrophoresis techniques on agarose gel can separate protein constituents contained in samples, in particular biological samples such as serum, blood, urine, cereprospinal fluid, etc. In a medium in the form of a gel and containing a buffer solution, proteins deposited on the gel surface ionise and migrate at different rates depending on their respective charge under the effect of an electric field. The thinness of the bands obtained after electrophoresis, corresponding to the separated constituents of the sample and hence the resolving power of the procedure, depends mainly on the thinness of the loading of the sample.

Different types of sample applicators can be used to improve the thinness of the loading. Such applicators, often termed sample combs, can take a number of different forms, as illustrated by the following devices:

"Groove" combs where the teeth carry a groove the edges of which are parallel to the plane of application, which means that a drop of biological sample can be taken by capillary action. The comb is then applied to the electrophoresis gel under the effect of its own weight. The teeth are then in contact with the gel surface and the sample is transferred from the tooth to the gel. Such combs can be formed from a metallic or plastics material.

"Strip" combs, whose principle is identical to that of groove combs, but the teeth of which comprise two parallel strips disposed at their extremity in a plane perpendicular to the plane of application. The sample is taken by capillary action into the space delimited by the two strips and loaded on the gel in the same manner as when using a groove comb. As before, such combs can be formed from a metallic or plastics material.

Membrane combs whose teeth are constituted by a microporous membrane. Such combs have been described in European patents EP-A-0 493 996 and in U.S. Pat. Nos. 5,464,515 and 5,405,516. The teeth are impregnated with the sample until the microporous membrane is saturated. The teeth of the comb are then brought into contact with the gel surface in the same manner as in the above two cases. In this case, the sample is loaded by diffusion of the proteins from the microporous membrane towards the gel.

Such different applicator types can all produce thin loading at a greater or lesser efficiency.

The sample is usually diluted when carrying out electrophoresis, in particular for immunofixation. The most routinely used dilutions are from ⅓ to ¹⁄₁₀. In general, the diluting solution is physiological water to keep the proteins in solution. After applying the diluted sample to the gel using an applicator as described above for an average period of 30 seconds to 120 seconds, preferably 60 seconds to 120 seconds depending on the applicator and the dilution of the sample, the location where the tooth comes into contact with the gel is observed to exhibit a compression mark which does not disappear during migration. After the staining step, this compression mark results in an absence of staining or a reduction in the intensity of staining described above.

Considering their weight (from a few grams to tens of grams, depending on the embodiment), application of such combs to the gel surface compresses the gel at the location where the teeth are in contact with the gel, resulting in a deformation in the form of a compression mark on the surface. If care is not taken, this deformation subsists during migration and becomes visible after staining the gel, which is carried out to reveal the electrophoretic profile. That deformation results in a zone, which is less, stained or not stained which can be considerably deleterious to interpretation of the electrophoregram.

SUMMARY OF THE INVENTION

The aim of the invention is to provide a means for eliminating this loading mark whatever the type of applicator used.

The inventors have observed that the loading mark produced on the electrophoresis support, in particular on the gel, can be eliminated or at the very least neutralised so that it does not affect the interpretation of the results obtained following electrophoresis, by hydrating the electrophoresis support at the sample loading zone compressed by application of the sample applicator. This hydration must be carried out under conditions enabling the constituents, and in particular the proteins contained in the sample being tested, to penetrate into this electrophoresis support zone to undergo electrophoretic migration.

Thus the electrophoresis support zone compressed by the applicator used to load the sample has to be re-hydrated sufficiently rapidly and effectively for the constituents of the sample to be able to penetrate into the electrophoresis support and migrate under the applied electric field.

When electrophoresis is carried out over a certain period of time, hydration must occur in a period corresponding to 10% to 20% of that electrophoresis period (this latter corresponding to the period during which a voltage is applied to the electrophoresis support), timed from application of the voltage to the electrophoresis support. Advantageously, re-hydration can occur more rapidly, i.e., within a period less than 10% of the electrophoresis period, timed from application of the voltage.

The inventors have identified certain compounds which, when introduced into the sample diluent and thus loaded onto the electrophoresis support at the same time as the sample, are capable of causing the clear mark left by compression of the electrophoresis support to disappear. These compounds remove or at least attenuate this distinct mark from the first moments of electrophoretic migration, while this mark persists throughout migration in the absence of said compounds.

The inventors have observed that these compounds cause the electrophoresis support to re-swell at the location marked by loading the sample, resulting from rapid re-hydration of the compressed zone.

The invention thus provides a composition for use in a process for separating the constituents of a sample by electrophoresis on an electrophoresis support, comprising one or more ionic compounds which, on application of an electric field to an electrophoresis support having negative surface charges, causes hydration of the loading zone of the sample to be separated, when said zone exhibits a compression mark resulting from loading the sample. This compression results from the pressure exerted by the applicator on the support.

The presence of negative surface charges on the electrophoresis support is the sign of non-zero electroendosmosis (or electroosmotic flow).

Compression of the electrophoresis support resulting from loading the sample using an applicator can be observed with the naked eye and corresponds to a compression mark on the support. Such a mark can, for example, be described as being V shaped, generally with a depth of less than 100μ and with a width of about 1 mm between the two top portions of the V for an electrophoresis support constituted by a 0.8% agarose gel, when the pressure of the applicator is more than 0.1 g/mm².

Depending on the case, the ionic compounds used to prepare the composition of the invention can be displaced or remain essentially immobile during electrophoretic migration.

The absence of displacement in the electric field is attributable either to the nature of the compound or to its concentration in the composition, or to a combination of these factors.

For a given electrophoresis support, in particular one where the electroendosmosis index (–rm index, relative mobility index) is known, the concentration of ionic compounds present in the composition is determined as a function of the nature of these compounds, in particular their capacity or otherwise to migrate in the electrophoresis support after application of the electric field. This concentration must be selected so as to enable hydration of the sample loading zone in the electrophoresis support from the first moments of electrophoretic migration.

As indicated above, the desired hydration or re-hydration effect of the electrophoresis support depends on the nature of the ionic compounds used, and can also be influenced by the composition of the electrophoresis support and in particular its electroendosmosis index.

In this regard, when the electrophoresis support is an agarose gel, to enable a sufficient addition of water during migration, in particular in the gel compression zone, agarose gels with a non zero electroosmotic flow are used, for example corresponding to a relative mobility index, –rm, of 0.07 or more.

The ionic compounds used in the present invention are dissolved to form the composition defined above. They are used in a set concentration, which is below their solubility limit.

DESCRIPTION OF THE PREFERRED EMBODIMENTS

In a first embodiment of the invention, the composition comprises one or more ionic compounds selected from those, which do not undergo substantial displacement in an electric field.

Thus these compounds can re-hydrate the compressed electrophoresis support zone but do not migrate with the constituents of the sample during electrophoresis.

The invention advantageously provides a composition comprising one or more ionic compounds selected from zwitterionic compounds.

Examples of zwitterionic compounds, which can be cited in the context of the present invention, are amino acid type zwitterionic compounds or zwitterionic buffers.

As an example, the composition of the invention can be produced using amino acids with formula $NH_2$—R—COOH, where R comprises an uncharged polar side chain.

In another embodiment of the invention, the amino acids selected can be amino acids with formula $NH_2$—R—COOH, where R comprises a basic side chain.

The amino acids satisfying one or other of the above definitions can be used alone or, possibly as a mixture, optionally mixed with other compounds, which may be ionic or non ionic, usable to re-hydrate the electrophoresis support when this support can undergo electroendosmosis.

Examples of amino acids, which are suitable for preparing the composition of the invention, which can be cited, are: glycine (preferably in a concentration which is compatible with its solubility in water at 25° C.; in this respect a concentration in the range of 1 M to 3.33 M can be used), and phenylalanine in a concentration of 0.28 M.

Other examples are amino acids selected from L-lysine advantageously in a concentration of 1 M or more, L-arginine preferably in a concentration in the range of 0.45 M to 0.86 M, and L-histidine, preferably in a concentration of 0.27 M.

Examples of zwitterionic buffers, which can be cited for use in the present invention in a concentration of more than 0.3 M and within the limit of their solubility, are the following biological buffers or their salts:

TRICINE (N-tris(hydroxymethyl)methyl-glycine);
HEPES (N-(2-hydroxyethyl)piperazine-N'-(2-ethane sulphonic acid));
PIPES (piperazine-N-N'-bis(2-ethane sulphonic acid);
MOPS (3-(N-morpholino)propane sulphonic acid);
TAPS (N-tris(hydroxymethyl)methyl-3-aminopropane sulphonic acid);
AMPSO (3-((1,1-dimethyl-2-hydroxyethyl)amino)-2-hydroxy-propane sulphonic acid)
TES (N-tris(hydroxymethyl)methyl-2-aminoethane sulphonic acid);
BES (N,N'-bis(2-hydroxyethyl)-2-aminoethane sulphonic acid);
BICINE (5N,N-bis(2-hydroxyethyl)glycine);
CHES (2-(N-cyclohexylamino)ethane sulphonic acid);
DIPSO (3-(N,N-bis(2-hydroxyethyl)amino)-2-hydroxy-propane sulphonic acid;
EPPS (N-(2-hydroxyethyl)piperazine-N'-(3-propane sulphonic acid));
MOPSO (3-(N-morpholino)propane sulphonic acid);
POPSO (piperazine-N,N'-bis(2'hydroxypropane sulphonic acid));
MES (2-morpholinoethane sulphonic acid).

Alternatively, the inventors have observed that the desired re-hydration effect of the electrophoresis support from the first moments of sample migration can be obtained with ionic compounds, which can undergo electrophoretic migration, provided that these compounds are present in a concentration, which is sufficient such that despite their migration, the electrophoresis support can hydrate at the sample loading zone. Such compounds are, for example, salts used in a high concentration and in particular in a concentration determined using routine procedures, taking the mobility of the anion into account. The lower the mobility of the anion, the lower the effective concentration of the salt.

By way of example, these salts can be selected from NaCl, KCl or $NaHCO_3$ in a concentration of 1 M or more, or a boric acid salt in a concentration of 0.15 M or more, or a phosphoric acid salt or an acetic acid salt in a concentration of 0.5 M or more.

The invention thus concerns the use of a composition satisfying one of the definitions given above, or several of these definitions in combination, for hydrating an electrophoresis support in the zone where the sample to be separated by electrophoresis is loaded.

This use can be by way of diluting the sample to be separated by electrophoresis using the composition of the invention.

The invention also provides a kit for carrying out a process for separating sample constituents by electrophoresis, characterized in that it comprises:

a composition as defined above;

an electrophoresis support constituted by a gel with a non zero electroosmotic flow.

Such a kit can also comprise any other reagent or device, which is normally present in electrophoresis kits, such as migration buffers, and revealing agents used to identify the constituents separated from the sample by electrophoresis.

An electrophoresis support, which can be used in the present invention is generally a gel and in particular a gel with a non zero electroosmotic flow.

Examples which can be cited are agarose gels, in particular HGT® or HEEO® agarose gels from FMC-BIOWHITTAKER or LE® or SHE® agaroses from HISPANAGAR, or mixtures thereof.

These agarose gels have non-zero electroendosmosis. The concentration of the agarose gels used to prepare the electrophoresis supports of the invention is 0.8% to 1% of agarose, and may contain mixtures of agaroses.

The invention also concerns a process for separating the constituents of a sample by electrophoresis, comprising:

loading a sample the constituents of which are to be separated onto an electrophoresis support, using an applicator;

simultaneously with loading the sample, loading a composition as defined above onto an electrophoresis support;

applying an electric field to enable the sample constituents to migrate;

revealing the constituents separated by electrophoresis.

Revealing can be carried out using stains and in the case of immunofixation, using antiserums and stains.

The process defined above can be carried out using routine electrophoresis methods and can in particular comprise an immunofixation procedure to reveal the constituents separated by electrophoresis.

In particular, the process of the invention employing the composition defined above can be effectively used to detect the presence of para-proteins in a biological sample.

This process can advantageously be carried out within the context of zone electrophoresis separation.

When carrying out the process of the invention, simultaneous loading of the sample and the composition of the invention enable the gel to re-hydrate in the very first moments of electrophoretic migration.

To carry out a simultaneous loading, the sample and the composition of the invention can be combined, prior to loading onto the electrophoresis support, in particular by diluting the sample in the composition.

Further features and advantages of the invention will become clearer from the following examples.

EXAMPLE 1

Typing Serous Para-proteins Diluted in a Tricine Solution (0.45 M) on an Immunofixation Gel 0.32 g of tricine was dissolved in 4 ml of water in a test tube. The diluent thus constituted is ready for use. The serous sample to be typed was diluted in the diluent to one third for the lane corresponding to the electrophoretic profile, as well as for the IgA, IgM, IgK and Igλ lanes (for example, 30 μl of serum and 60 μl of diluent) and to one sixth for the IgG revealing lane (for example 20 μl of serum and 100 μl of diluent).

4 ml of physiological water was introduced into another test tube to dilute the same sample in an identical manner to that above.

10 μl of diluted sample were charged into each well of the membrane applicator described in EP-A-0 493 996, U.S. Pat. Nos. 5,464,515 and 5,405,516. This charged applicator was then applied to the IF gel surface for 1 minute.

The samples applied to the IF gel were separated by electrophoresis for about 10 minutes at a power of 20 W using an instrument which regulated the temperature at 20° C.

After migration, the para-proteins were typed by incubating each migration lane with a specific antiserum (anti IgG, anti IgA, anti IgM, anti IgK, anti Igλ) and the lane corresponding to the electrophoretic profile with a protein fixing solution. The excess reagent was eliminated, and the gel was dried and stained with acid violet.

The samples diluted in tricine were observed to exhibit no mark on the gel at the location of loading while the gel of those diluted with physiological water exhibited a strong imprint of the applicator.

EXAMPLE 2

Typing Serous Para-proteins Diluted in an Arginine Solution (0.86 M) on an Immunofixation Gel 0.6 g of L-arginine was dissolved in 4 ml of water in a test tube. The diluent thus constituted is ready for use. The serous sample to be typed was diluted in the diluent to one third for the lane corresponding to the electrophoretic profile, as well as for the IgA, IgM, IgK and Igλ lanes (for example, 30 μl of serum and 60 μl of diluent) and to one sixth for the IgG revealing lane (for example 20 μl of serum and 100 μl of diluent).

4 ml of physiological water was introduced into another test tube to dilute the same sample in an identical manner to that above.

10 μl of diluted sample were charged into each well of the membrane applicator described in EP-A-0 493 996, U.S. Pat. Nos. 5,464,515 and 5,405,516. This charged applicator was then applied to the IF gel surface for 1 minute.

These samples applied to the IF gel were separated by electrophoresis for about 10 minutes at a power of 20 W using an instrument which regulated the temperature at 20° C.

After migration, the para-proteins were typed by incubating each migration lane with a specific antiserum (anti IgG, anti IgA, anti IgM, anti IgK, anti Igλ) and the lane corresponding to the electrophoretic profile with a protein fixing solution. The excess reagent was eliminated, and the gel was dried and stained with acid violet.

The samples diluted in arginine were observed to exhibit no mark on the gel at the location of loading while the gel of those diluted with physiological water exhibited a strong imprint of the applicator.

EXAMPLE 3

Typing Serous Para-proteins Diluted in a Sodium Chloride Solution (1.2 M) on an Immunofixation Gel 0.29 g of NaCl was dissolved in 4 ml of water in a test tube. The diluent thus constituted is ready for use. The serous sample to be typed was diluted in the diluent to one third for the lane corresponding to the electrophoretic profile, as well as for the IgA, IgM, IgK and Igλ lanes (for example, 30 μl of serum and 60 μl of diluent) and to one sixth for the IgG revealing lane (for example 20 μl of serum and 100 μl of diluent).

4 ml of physiological water was introduced into another test tube to dilute the same sample in an identical manner to that above.

10 μl of diluted sample were charged into each well of the membrane applicator described in EP-A-0 493 996, U.S. Pat. Nos. 5,464,515 and 5,405,516. This charged applicator was then applied to the IF gel surface for 1 minute.

The samples applied to the IF gel were separated by electrophoresis for about 10 minutes at a power of 20 W using an instrument which regulated the temperature at 20° C.

After migration, the para-proteins were typed by incubating each migration lane with a specific antiserum (anti IgG, anti IgA, anti IgM, anti IgK, anti Igλ)) and the lane corresponding to the electrophoretic profile with a protein fixing solution. The excess reagent was eliminated, and the gel was dried and stained with acid violet.

The samples diluted in the concentrated NaCl solution were observed to exhibit no mark on the gel at the location of loading while those diluted with physiological water exhibited a strong imprint of the applicator.

What is claimed is:

1. A process for reswelling a portion of an electrophoresis support comprising: introducing to a loading zone of said electrophoresis support a composition including at least one ionic compound capable of reswelling a compressed portion of said loading zone.

2. The process of claim 1 further comprising: adding said composition to a sample to be separated by electrophoresis prior to introducing said composition to said electrophoresis support.

3. The process of claim 1 or 2, wherein said ionic compound will remain essentially immobile during electrophoretic migration.

4. The process of claim 3, wherein said ionic compound is zwitterionic.

5. The process of claim 4, wherein said zwitterionic compound is an amino acid or zwitterionic buffer.

6. The process of claim 5, wherein said compound capable of reswelling a compressed portion of said loading zone is an amino acid of the formula $NH_2$—R—COOH, and wherein R comprises an uncharged polar side chain.

7. The process of claim 5, wherein said compound capable of reswelling a compressed portion of said loading zone is an amino acid of the formula $NH_2$—R—COOH, and wherein R comprises a basic side chain.

8. The process of claim 5, wherein said amino acid is glycine, present in a concentration which is compatible with its solubility in water at 25° C., or phenylalanine in a concentration of about 0.28 M.

9. The process of claim 5, wherein said amino acid is selected from lysine in a concentration of at least about 1 M, arginine in a concentration in the range of about 0.45 M to about 0.86 M, and histidine in a concentration of at most about 0.27 M.

10. The process of claim 5 wherein said zwitterionic buffer is provided in a concentration that is about 0.3 M or greater.

11. The process of claim 10, wherein said zwitterionic buffer is:

TRICINE (N-tris(hydroxymethyl)methyl-glycine);

HEPES (N-(2-hydroxyethyl)piperazine-N'-(2-ethane sulphonic acid));

PIPES (piperazine-N-N'-bis(2-ethane sulphonic acid);

MOPS (3-(N-morpholino)propane sulphonic acid);

TAPS (N-tris(hydroxymethyl)methyl-3-aminopropane sulphonic acid);

AMPSO (3-((1,1-dimethyl-2-hydroxyethyl)amino)-2-hydroxy-propane sulphonic acid)

TES (N-tris(hydroxymethyl)methyl-2-aminoethane sulphonic acid);

BES (N,N'-bis(2-hydroxyethyl)-2-aminoethane sulphonic acid);

BICINE (5N,N-bis(2-hydroxyethyl)glycine);

CHES (2-(N-cyclohexylamino)ethane sulphonic acid);

DIPSO (3-(N,N-bis(2-hydroxyethyl)amino)-2-hydroxy-propane sulphonic acid;

EPPS (N-(2-hydroxyethyl)piperazine-N'-(3-propane sulphonic acid));

MOPSO (3-(N-morpholino)propane sulphonic acid);

POPSO (piperazine-N,N'-bis(2'hydroxypropane sulphonic acid));

MES (2-morpholinoethane sulphonic acid); or a salt thereof.

12. The process of claim 1 or 2, wherein said ionic compound will migrate during electrophoretic migration.

13. The process of claim 12, wherein said ionic compound is a salt.

14. The process of claim 13, wherein said salt is selected from NaCl, KCl or $NaHCO_3$ in a concentration of at least about 1 M, or a boric acid salt in a concentration of at least about 0.15 M, or a phosphoric acid salt or an acetic acid salt in a concentration of at least about 0.5 M.

15. The process of claim 1 wherein said at least one ionic compound capable of reswelling a compressed portion of said loading zone is selected and is provided in a concentration which is sufficient to achieve reswelling in a period of at most about 20% of the period which a voltage is applied to said electrophoresis support.

16. The process of claim 15 wherein said at least one compound capable of reswelling a compressed portion of said loading zone is selected and is provided in a concentration which is sufficient to achieve reswelling in a period of at most about 10% of the period which a voltage is applied to said electrophoresis support.

17. An electrophoresis process for separation of at least one constituent of a sample, comprising the steps of:

a) loading a sample onto a loading zone of an electrophoresis support;

b) loading a composition onto said loading zone said composition including at least one compound capable of reswelling a compressed portion of said loading zone;

c) applying an electric field to said support enabling said at least one sample constituent to migrate.

18. The process of claim 17 further comprising the step of: revealing said at least one constituent of said sample separated by electrophoresis.

19. The process of claim 17, wherein said sample is applied to said support using an applicator thereby creating said compressed portion of said loading zone.

20. The process of claim 19, wherein said sample and said composition are loaded onto said loading zone substantially simultaneously.

21. The process of claim 20, wherein said composition and said sample are mixed prior to loading onto said loading zone.

22. The process of claims 17 or 21 wherein said compound capable of reswelling said compressed portion of said loading zone is an ionic compound, which will remain essentially immobile during electrophoretic migration.

23. The process of claim 22, wherein said at least one compound capable of reswelling said compressed portion of said loading zone is zwitterionic.

24. The process of claim 23, wherein said zwitterionic compound is an amino acid or zwitterionic buffer.

25. The process of claim 24, wherein said compound capable of reswelling a compressed portion of said loading zone is an amino acid of the formula $NH_2$—R—COOH, and wherein R comprises an uncharged polar side chain.

26. The process of claim 24, wherein said compound capable of reswelling a compressed portion of said loading zone is an amino acid of the formula $NH_2$—R—COOH, and wherein R comprises a basic side chain.

27. The process of claim 24, wherein said amino acid is glycine, present in a concentration which is compatible with its solubility in water at 25° C., or phenylalanine in a concentration of about 0.28 M.

28. The process of claim 24, wherein said amino acid is amino acid is selected from lysine in a concentration of at least about 1 M, arginine in a concentration in the range of about 0.45 M to about 0.86 M, and histidine in a concentration of at most about 0.27 M.

29. The process of claim 24, wherein said zwitterionic compound is a zwitterionic buffer provided in a concentration that is about 0.3 M or greater.

30. The process of claim 24, wherein said zwitterionic buffer is:

TRICINE (N-tris(hydroxymethyl)methyl-glycine);

HEPES (N-(2-hydroxyethyl)piperazine-N'-(2-ethane sulphonic acid));

PIPES (piperazine-N-N'-bis(2-ethane sulphonic acid);

MOPS (3-(N-morpholino)propane sulphonic acid);

TAPS (N-tris(hydroxymethyl)methyl-3-aminopropane sulphonic acid);

AMPSO (3-((1,1-dimethyl-2-hydroxyethyl)amino)-2-hydroxy-propane sulphonic acid)

TES (N-tris(hydroxymethyl)methyl-2-aminoethane sulphonic acid);

BES (N,N'-bis(2-hydroxyethyl)-2-aminoethane sulphonic acid);

BICINE (5N,N-bis(2-hydroxyethyl)glycine);

CHES (2-(N-cyclohexylamino)ethane sulphonic acid);

DIPSO (3-(N,N-bis(2-hydroxyethyl)amino)-2-hydroxypropane sulphonic acid;

EPPS (N-(2-hydroxyethyl)piperazine-N'-(3-propane sulphonic acid));

MOPSO (3-(N-morpholino)propane sulphonic acid);

POPSO (piperazine-N,N'-bis(2'hydroxypropane sulphonic acid));

MES (2-morpholinoethane sulphonic acid); or a salt thereof.

31. The process of claim 17 or 21, wherein said at least one compound capable of reswelling said compressed portion of said loading zone is an ionic compound which will migrate during electrophoretic migration.

32. The process of claim 31, wherein said at least one compound capable of reswelling said compressed portion of said loading one is a salt.

33. The process of claim 32, wherein said salt is selected from NaCl, KCl or $NaHCO_3$ in a concentration of at least about 1 M, or a boric acid salt in a concentration of at least about 0.15 M, or a phosphoric acid salt or an acetic acid salt in a concentration of at least about 0.5 M.

34. The process of claim 17, wherein said at least one compound capable of reswelling a compressed portion of said loading zone is selected and is provided in a concentration which is sufficient to achieve reswelling in a period of at most about 20% of the period which a voltage is applied to said electrophoresis support.

35. The process of claim 34, wherein said at least one compound capable of reswelling a compressed portion of said loading zone is selected and is provided in a concentration which is sufficient to achieve reswelling in a period of at most about 10% of the period which a voltage is applied to said electrophoresis support.

* * * * *

UNITED STATES PATENT AND TRADEMARK OFFICE
CERTIFICATE OF CORRECTION

PATENT NO. : 6,572,746 B1
DATED : June 3, 2003
INVENTOR(S) : Georges Nouadje and Laurent Vincent It is certified that error appears in the above-identified patent and that said Letters Patent is hereby corrected as shown below:

<u>Column 8,</u>
Line 43, after "zone" insert -- , --.

<u>Column 9,</u>
Line 15, delete "is".
Line 16, delete "amino acid".

<u>Column 10,</u>
Line 20, "one" should read -- zone --.

Signed and Sealed this

Second Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,572,746 B1 Page 1 of 1
DATED : June 3, 2003
INVENTOR(S) : Georges Nouadje and Laurent Vincent It is certified that error appears in the above-identified patent and that said Letters Patent is hereby corrected as shown below:

<u>Title page,</u>
Item [57], ABSTRACT, delete the existing Abstract and insert the following:
-- A composition is used to enhance proper electrophoretic separation of a sample on a gel by re-swelling the compression mark formed when loading a sample onto the gel. The composition has one or more ionic compounds which aid in hydrating the loading zone when applying an electric field to the electrophoretic support. --

Signed and Sealed this

Eighth Day of June, 2004

JON W. DUDAS
*Acting Director of the United States Patent and Trademark Office*